United States Patent [19]
Olson

[11] Patent Number: 5,206,956
[45] Date of Patent: May 4, 1993

[54] PROTECTIVE FACE SHIELD

[76] Inventor: David V. Olson, 929 Medical Arts Bldg., Minneapolis, Minn. 55402

[21] Appl. No.: 772,347

[22] Filed: Oct. 7, 1991

[51] Int. Cl.$^5$ ............................................. A61F 9/00
[52] U.S. Cl. ................................................ 2/13; 2/9; 128/857
[58] Field of Search ................ 128/201.22, 201.23, 128/206.12, 206.21, 207.11, 857, 866; 2/9, 10, 11, 12, 13, 15, 424, 185 R, 199

[56] References Cited

U.S. PATENT DOCUMENTS

| | | | |
|---|---|---|---|
| 3,023,418 | 3/1962 | Hammond | 2/13 |
| 3,237,204 | 3/1966 | Honsaker | 2/13 |
| 3,298,031 | 1/1967 | Morgan | 2/9 |
| 3,392,463 | 7/1968 | Hachigian | 2/13 X |
| 3,991,753 | 11/1976 | Viesca | 2/9 X |
| 4,850,049 | 7/1989 | Landis et al. | 2/10 |
| 4,852,185 | 8/1989 | Olson | 2/9 |
| 4,853,974 | 8/1989 | Olim | 2/9 |
| 4,864,653 | 9/1989 | Landis | 2/9 |
| 4,867,178 | 8/1989 | Smith | 128/858 |
| 4,872,465 | 10/1989 | Kuntz et al. | 2/9 X |
| 4,884,296 | 12/1989 | Nix | 2/11 |
| 4,944,039 | 7/1990 | Dietrich | 2/13 |
| 4,944,312 | 7/1990 | Smith | 2/9 X |
| 4,965,887 | 10/1990 | Paeluccio et al. | 2/9 |

Primary Examiner—Werner H. Schroeder
Assistant Examiner—Jeanette E. Chapman

[57] ABSTRACT

A one-piece protective face shield intended primarily for use by health care professionals to reduce the transmission of infectious diseases carried by viral and bacterial emissions from the noses and throats of afflicted patients. The protective face shield comprises a generally flat semi-rigid transparent sheet which may be bent into a semi-cylindrical face-covering shape and suspended from the bows of the frames of the eyeglasses of the user. A pair of integral bow-engaging clips are provided adjacent to the top end edges of the transparent sheet. The transparent sheet clipped to the eyeglass bows is closely spaced from the user's face and forms a barrier to the transmission of disease causing organisms.

8 Claims, 2 Drawing Sheets

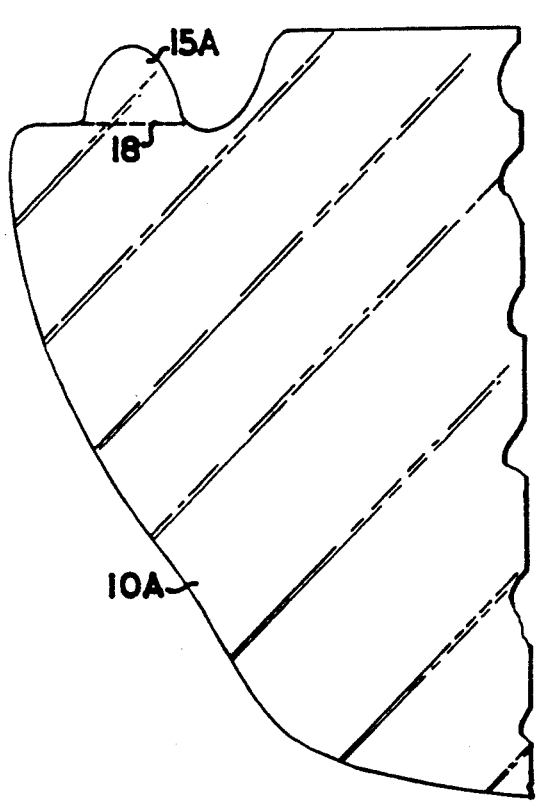
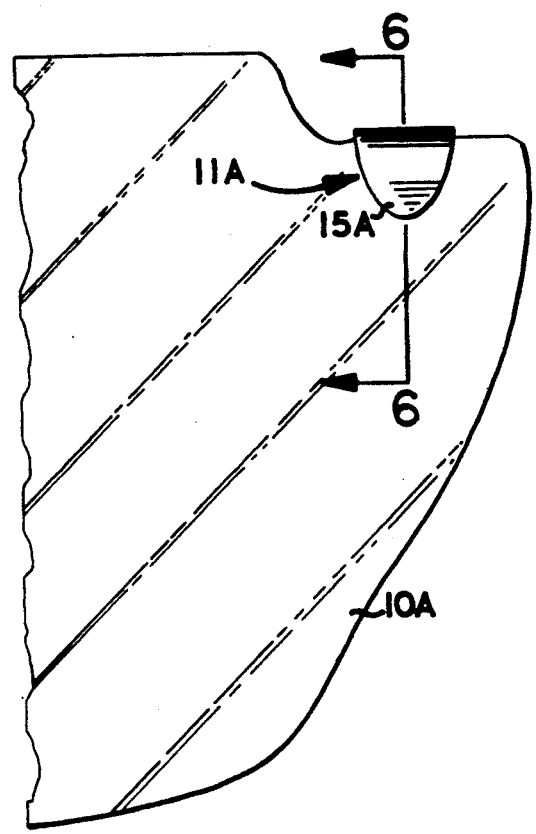
FIG. 4    FIG. 5
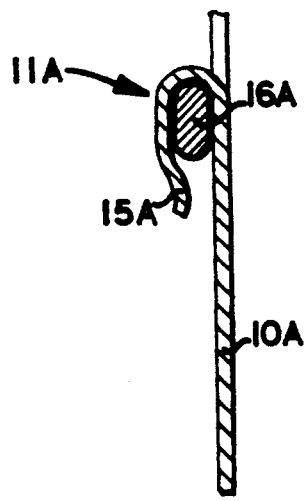
FIG. 6

PROTECTIVE FACE SHIELD

BACKGROUND OF THE INVENTION

1. Field of the Invention

This invention is directed to a simple inexpensive one-piece protective device for shielding the face of its wearer from flying particles, splashed liquids, aerosol emissions, and the like. The one-piece protective face shield according to the present invention is intended primarily as a simple inexpensive disposable device for use by health care professionals against the transmission of viral and bacterial diseases such as upper respiratory infections, acquired immune deficiency syndrome (AIDS), herpes simplex, hepatitis B, tuberculosis, and the like. Dentists, dental technicians, rhinologists, pharyngologists, and similar health care specialists who are exposed to nasal and/or oral emissions and secretions are especially susceptible. Although intended primarily for use by such health care professionals, the protective face shield of the present invention may be used to protect the face and eyes from metallic particles, rock chips, dust, paint splatters, and the like, generated in the course of carrying out a myriad of household and industrial tasks.

2. The Prior Art

Concern about the growing AIDS epidemic and fears of both health professionals and patients has created a demand for lighter, less expensive and preferably disposable face shields to replace face masks commonly used by health care professionals in combination with safety glasses or goggles, and the adaptions available for use in the health care field of relatively expensive bulky heavy duty face shields as are available in the market for such persons as welders, bicyclists and motorcyclists, and the like. Exemplary recent U. S. patents directed toward meeting this need are Landis, et al U.S. Pat. No. 4,850,049; Olson U.S. Pat. No. 4,852,185; Landis U.S. Pat. No. 4,864,653; Smith U.S. Pat. No. 4,867,178; Nix U.S. Pat. No. 4,884,296; and Paoluccio, et al U.S. Pat. No. 4,965,887. Although the latter patent discloses the concept of supporting a protective face shield from the eyeglass frames of the user, the shields of that patent utilize rubber lined spring clips or adjustable screw clips. The added cost of these clips and the assembly of the clips onto the face shield are expenses which raise the cost of the face shield to a level which encourages re-use and possible increased risk of contamination, thus partially defeating the purpose for which the shields are used.

SUMMARY OF THE INVENTION

It is the principal object of the present invention to provide a simple lightweight inexpensive one-piece disposable face shield which may be discarded or recycled after use. Broadly stated, the protective face shield according to the present invention comprises a generally flat semi-rigid transparent sheet which may be bent into a semi-cylindrical face-covering shape and suspended from the bows of the frames of the eyeglasses of the user by means of a pair of integral bow engaging clips formed in the body of the transparent sheet adjacent to the top end edges of that sheet.

BRIEF DESCRIPTION OF THE DRAWINGS

The invention is illustrated in the accompanying drawings in which corresponding parts are identified by the same numerals and in which:

FIG. 4 is a fragmentary plan view of a face shield showing an alternative form of clip prior to shaping;

FIG. 5 is a similar fragmentary plan view showing the alternative form of clip; and FIG. 6 is a section on an enlarged scale on the line 6—6 of FIG. 5 and in the direction of the arrows.

DETAILED DESCRIPTION OF THE PREFERRED EMBODIMENT

Figure 1:
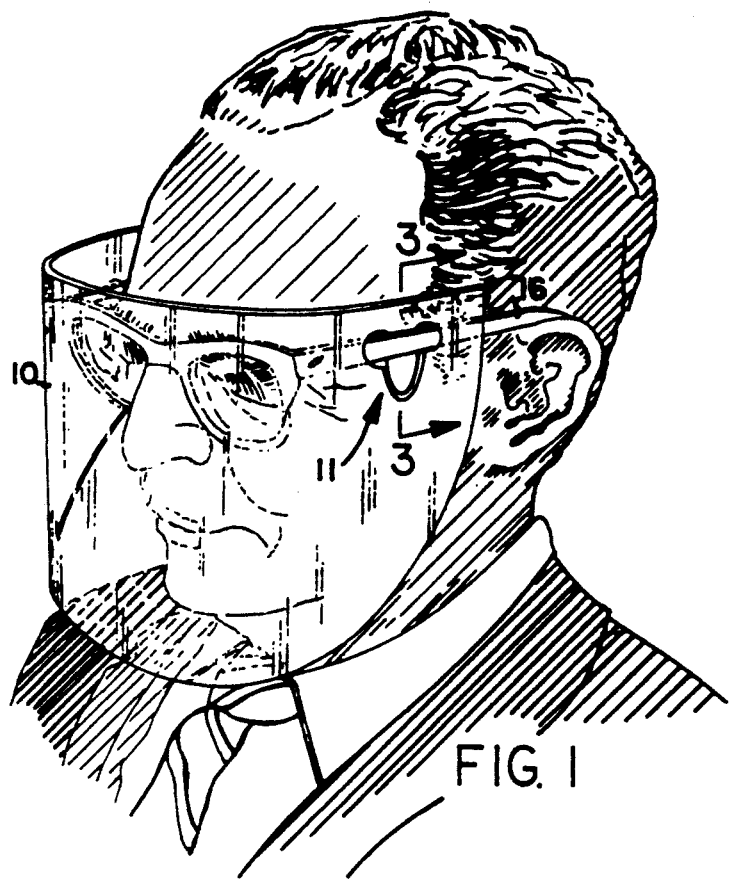
FIG. 1 is a left side elevation showing the protective face shield in use over the face of a person to be protected.
Figure 3:
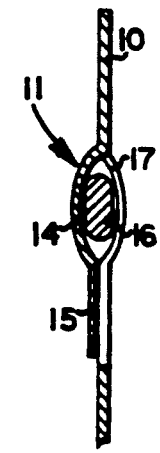
FIG. 3 is a section on an enlarged scale on the line 3—3 of FIG. 1 and in the direction of the arrows.
Figure 2:
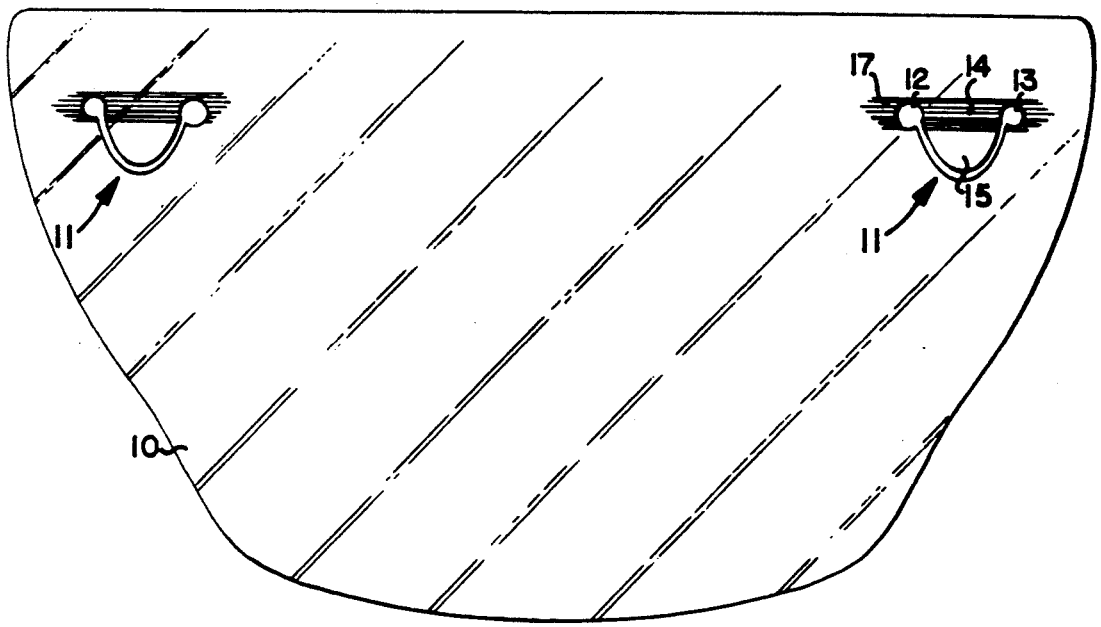
FIG. 2 is a plan view of the face shield.

Referring now to the drawings, and particularly to FIGS. 1 to 3, the one-piece protective face shield of the present invention comprises a thin lightweight sheet 10 of semi-rigid bendable transparent material. Although sheet 10 is illustrated as having a generally inverted trapezoidal configuration, its shape may vary widely. It must be of a size to substantially cover the face of the user, preferably extending to below the chin. The top edge may be extended to provide additional protection for the forehead. Typically it has an overall length between about 12 and 16 inches and an overall width between about 7 and 10 inches. The transparent sheet material may be composed, for example, of transparent lightweight synthetic resinous plastic such as polycarbonate, polypropylene, polyethylene, polyvinyl chloride, or the like. Preferably it has a thickness between about 0.01 to 0.015 inch.

As seen in FIG. 2, the protective face shield of the present invention is used by supporting it from the bows of the eyeglass frame of the wearer. If the user does not require eyeglassses for correction of vision, the shield may be supported from the bows of lens-less frames. To support the shield a pair of integral mirror image clips, indicated generally at 11, are formed adjacent to the top end edges of the transparent sheet 10. Clips 11 are formed, for example, by punching or die-cutting and each includes a pair of generally horizontally aligned spaced apart apertures 12 and 13. Apertures 12 and 13 are preferably spaced apart about 1 to 1.5 inch. A shallow longitudinal channel 14 is formed in the transparent sheet between apertures 12 and 13. Channel 14 corresponds in width to a size to receive the typical width of eyeglass bows currently in use, and in depth to the thickness of such bows. Because eyeglass bows generally taper slightly from the hinges connecting them to the body of the frame, inner apertures 12 are preferably slightly larger in diameter than outer apertures 13. Thus, channel 14 is slightly tapered to better engage the bow. Typically, aperture 12 may be about ⅜ to ¼ inch in diameter and aperture 13 about 5/16 to 7/32 inch in diameter, with the differences in diameter being between about 1/16 to 1/32 inch. A flat dependent tab 15 extends from the lower edge of channel 14. Because of its inherent resiliency tab 15 can easily be pushed by a finger out of its normal position in the plane of sheet 10 to permit the clip 11 to be hooked over the eyeglass bow. As best seen in FIG. 3, tab 15 then returns toward its normal at-rest position to hold channel 14 in engagement with bow 16. Typically tab 15 is about 0.75 to 1 inch long. Optionally, tapering channels 17 may be formed in sheet 10 concaved in the opposite direction from channel 14 to further insure firm engagement between clips 11 and bows 16. As seen in FIG. 2, channels 17 extend longitudinally from apertures 12 and 13 in opposite directions spaced away from channel 14 and tab 15.

In normal use the face shield, with the convex side of channels 14 toward the user, is grasped with both hands and bent into semi-cylindrical shape. Tabs 15 are pushed inwardly to an angle of about 45 degrees and the clips 11 are readily engaged with the bows. The resiliency of the shield causes it to be positioned with the portions of the shield spaced inward from the clips in engagement with the corners formed by the hinges of the glasses frame. This four-point engagement of the shield with the frame insures its stability in use. The shield is sufficiently spaced from the user's face that air readily circulates behind it to prevent the accumulation of breath vapors which would fog the transparent sheet. The shield may extend substantially vertically and parallel relative to the face of the wearer. Preferably, however, the transparent member is canted inwardly toward the chin of the wearer for maximum protection. This may be accomplished by forming channels 14 so that they are slightly out of longitudinal alignment and tilted downwardly relative to the top edge in the direction toward the ends of the sheet 10. Typically the outermost apertures 13 may be spaced from the top edge of sheet 10 by about ⅛ to ¼ inch farther than the innermost apertures 12.

Referring now to FIGS. 4 to 6, there is shown an alternative form of one-piece protective face shield according to the present invention which comprises a thin lightweight sheet 10A of semi-rigid bendable transparent material, as already described. This form of face shield is used generally in the manner already described by supporting it from the bows of the eyeglass frame of the wearer. A pair of mirror image tabs 15A are provided extending upwardly from the top edge of transparent sheet 10A adjacent to the end edges of the sheet and generally in the plane thereof. Tabs 15A are bent back upon sheet 10A along fold line 18 and heat formed or otherwise shaped to form a clip 11A. Tabs 15A then lie generally in a second plane adjacent to and spaced slightly from sheet 10A and generally parallel thereto, as shown in FIG. 6. Clip 11A engages the bow 16A of a pair of eyeglasses generally in the manner already described. Typically tab 15A is about 1 to 1.5 inch wide and about 0.75 to 1 inch deep. The top center portion of transparent sheet 10A is preferably somewhat wider to provide additional protection for the forehead area of the user. This alternative form of protective face shield is used in the manner already described.

The protective shields acccording to the present invention are of extremely simple one-piece construction composed of inexpensive readily available material and they may be formed with a minimum of manufacturing operations. Because of this, the shields may be regarded as disposable after use in the examination and/or treatment of each individual patent. The shields are lightweight and comfortable to wear and are easily put on and removed.

It is apparent that many modifications and variations of this invention as hereinbefore set forth may be made without departing from the spirit and scope thereof. The specific embodiments described are given by way of example only and the invention is limited only by the terms of the appended claims.

What I claim as my invention is:

1. A simple inexpensive disposable one-piece protective face shield to cover the eyeglass frame and face of the user thereof, said shield comprising:
   A) a semi-rigid face-covering transparent sheet readily bendable into semi-cylindrical shape, said sheet having a body portion and a top edge with end portions, and front and back surfaces, and
   B) a pair of integral mirror image bow-engaging clips formed in the body of the transparent sheet adjacent to the top end edge portions thereof, each of said clips including:
      1) a pair of generally horizontally aligned spaced apart apertures formed in the transparent sheet;
      2) a shallow channel extending between said apertures, said channel having upper and lower edges; and
      3) a flat dependent bendable tab extending from the lower edge of said channel.

2. A face shield according to claim 1 wherein:
   A) said transparent sheet has a center and end edges; and
   B) the diameter of the aperture closest to the center of the transparent sheet is slightly larger than the aperture closest to the end edge of the sheet.

3. A face shield according to claim 2 wherein the diameter of the larger aperture is about ⅜ to ⅛ inch, and the diameter of the smaller aperture is between about 5/16 to 7/32 inch, and the difference in diameters is between about 1/16 and 1/32 inch.

4. A face shield according to claim 1 wherein said apertures are spaced apart about 1 to 1.5 inch and said tab extends from said channel about 0.75 to 1 inch.

5. A face shield according to claim 1 wherein tapering channels are provided in the transparent sheet, said tapering channels being concaved in the opposite direction from said first channel and extending longitudinally from said apertures in opposite directions spaced away from said channel between the apertures and said tab.

6. A face shield according to claim 1 wherein the clip channels are slightly out of longitudinal alignment and tilted downwardly relative to the top edge of the transparent sheet in the direction toward the ends of the sheet such that the outermost apertures are spaced from the top edge of the sheet by about 1/16 to 3/16 inch farther than the innermost apertures.

7. A simple inexpensive disposable one-piece protective face shield to cover the eyeglass frame and face of the user thereof, said shield comprising:
   A) a semi-rigid face-covering transparent sheet readily bendable into semi-cylindrical shape, said sheet having a body portion of a size to substantially cover the face of the user, and having a top edge with end portions, and front and back surfaces, and
   B) a pair of integral mirror image bow-engaging clips formed in the body of the transparent sheet adjacent to the top end edge portions thereof, each of said clips comprising a tab initially extending upwardly from the top edge of the transparent sheet and generally in the plane thereof, and then folded back and downwardly adjacent to the surface of the transparent sheet in a second plane spaced slightly from and generally parallel to the plane of the transparent sheet.

8. A face shield according to claim 7 wherein said folded back clip is about 1 to 1.5 inch wide and about 0.75 to 1 inch deep.

* * * * *